United States Patent
Johnson et al.

(10) Patent No.: US 10,117,836 B2
(45) Date of Patent: Nov. 6, 2018

(54) TABLET FORMULATION FOR CGRP ACTIVE COMPOUNDS

(71) Applicant: Merck Sharp & Dohme Corp., Rahway, NJ (US)

(72) Inventors: Mary Ann Johnson, West Point, PA (US); Leonardo Resende Allain, Lansdale, PA (US); W. Mark Eickhoff, Lansdale, PA (US); Craig B. Ikeda, Harleysville, PA (US); Chad D. Brown, Quakertown, PA (US); Francis J. Flanagan, Jr., North Wales, PA (US); Rebecca Nofsinger, Lansdale, PA (US); Melanie Marota, Lansdale, PA (US); Lisa Lupton, South San Francisco, CA (US); Paresh B. Patel, Langhorne, PA (US); Hanmi Xi, Furlong, PA (US); Wei Xu, North Wales, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/115,026

(22) PCT Filed: Jan. 30, 2015

(86) PCT No.: PCT/US2015/013672
§ 371 (c)(1),
(2) Date: Jul. 28, 2016

(87) PCT Pub. No.: WO2015/119848
PCT Pub. Date: Aug. 13, 2015

(65) Prior Publication Data
US 2016/0346214 A1 Dec. 1, 2016

Related U.S. Application Data (60) Provisional application No. 62/087,366, filed on Dec. 4, 2014, provisional application No. 61/936,019, filed on Feb. 5, 2014.

(51) Int. Cl.
*A61K 31/437* (2006.01)
*A61K 31/4545* (2006.01)
*A61K 9/20* (2006.01)

(52) U.S. Cl.
CPC .......... *A61K 9/2077* (2013.01); *A61K 9/2009* (2013.01); *A61K 9/2013* (2013.01); *A61K 9/2027* (2013.01); *A61K 9/2031* (2013.01); *A61K 9/2054* (2013.01); *A61K 31/437* (2013.01); *A61K 31/4545* (2013.01)

(58) Field of Classification Search
None
See application file for complete search history.

(56) References Cited

U.S. PATENT DOCUMENTS

2004/0076668 A1   4/2004   Berchielli et al.
2010/0227903 A1   9/2010   Geers et al.
2012/0122899 A1   5/2012   Bell et al.

FOREIGN PATENT DOCUMENTS

WO      2006069754 A1      7/2006
WO      WO-2012064910 A1 *   5/2012   ........... C07D 471/10

OTHER PUBLICATIONS

Ramadhani et al. "Preparation and Characterisation of KOL-LIPHOR P188 and P 237 Solid Dispersion Oral Tablets Containing the Poorly Water Soluble Drug Disulfiram". International Journal of Pharmaceutics. Sep. 2014 [Online], 475:514-522. (Year: 2014).*
Cho et al. "Development of Novel Fast-Dissolving Tacrolimus Solid Dispersion-Loaded Prolonged Release Tablet". European Journal of Pharmaceutical Sciences. Jan. 2014 [Online], 4:1-7. (Year: 2014).*
Anonymous: "Handbook of Pharmaceuticals Excipients", 2000, Pharmaceutical Press, XP002773202, p. 386.
Anonymous: "Remington, The Science and Practice of Pharmacy", 2000, Lippincott Williams&Wilkins, XP002773203, pp. 861-862.
Anonymous: "Handbook of Pharmaceutical Excipients", 2000, Pharmaceutical Press, XP002773225, p. 201.
International Search Report and Written Opinion of the International Searching Authority Application No. PCT/US15/13672 dated Jan. 30, 2015.

* cited by examiner

*Primary Examiner* — Leslie A. Royds Draper
(74) *Attorney, Agent, or Firm* — Mintz, Levin, Cohn, Ferris, Glovsky and Popeo, P.C.

(57) ABSTRACT

The present invention is directed to compositions comprising an extrudate or solid solution of a compound, or a salt thereof, of Formula I (API): Formula I, wherein "$R^a$" is independently H or —F, in a water-soluble polymer matrix which further comprises a disintegration system allowing a tablet made therefrom to rapidly disintegrate in the environment in which the API is to be released.

(I)

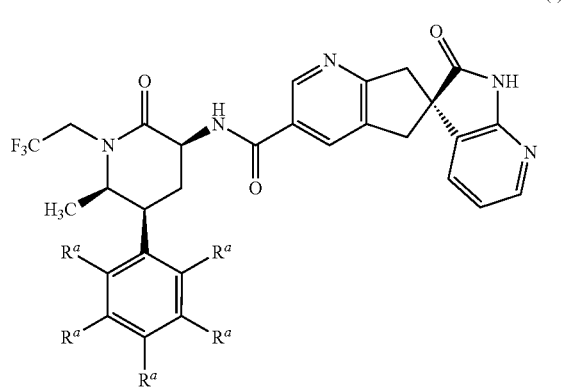

21 Claims, 3 Drawing Sheets

TABLET FORMULATION FOR CGRP ACTIVE COMPOUNDS

CROSS-REFERENCE TO RELATED APPLICATIONS

This application is a U.S. National Phase application under 35 U.S.C. § 371 of PCT Application No. PCT/US2015/013672, filed Jan. 30, 2015, which application in turn claims the priority of U.S. Provisional Patent Application Ser. No. 61/936,019 filed Feb. 5, 2014 and U.S. Provisional Patent Application Ser. No. 62/087,366 filed Dec. 4, 2014.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. Calcitonin gene-related peptide (CGRP) is a potent vasodilatory neurotransmitter believed to play a key role in migraine pathophysiology. The initial human clinical validation of the CGRP target was provided by Boehringer Ingelheim in 2003 with the report that an IV formulation comprising olcegepant was efficacious in the acute treatment of migraine and the mechanism was confirmed by a study using telcagepant (a CGRP antagonist) in an oral formulation.

Newly developed CGRP antagonist compounds are described in published international application, publication no. WO 2012/064910, which are based on the structure of Formula I:

Formula I where "$R^a$" is various substituents (for example, where "$R^a$" is hydrogen: (S)—N-((3S,5S,6R)-6-methyl-2-oxo-5-phenyl-1-(2,2,2-trifluoroethyl)piperidin-3-yl)-2'-oxo-1',2',5,7-tetrahydrospiro[cyclopenta[b]pyridine-6,3'-pyrrolo[2,3-b]pyridine]-3-carboxamide and, for example, where three of "$R^a$" are selected to be fluorine: (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide). These compounds show promise as well-tolerated, potent CGRP-antagonist with low potential for side effects and metabolic complications. However, these compounds have low solubility and in general do not form salts suitable for the preparation of a stable pharmaceutical formulation.

For initial in vivo study it is common to administer poorly-soluble "class II" compounds formulated as a liquid formulation, for example, as a cosolvent or lipid-based solution employing a cosolvent such as PEG400, and other constituents as needed, to facilitate dissolution and enhance oral absorption. Although useful for clinical studies, in general it is not commercially attractive to provide a liquid formulation for oral delivery of medications for use in therapy for acute or chronic conditions or for use in prophylaxis treatment of chronic conditions. Desirably, such medicaments should be in a solid form for oral administration, for example, a pressed tablet or a capsule containing the API. In general, however, drugs with poor aqueous solubility are difficult to deliver in the gastrointestinal system without some solubility enhancer or permeation enhancer, or both, present at the site of absorption.

Solid dispersions, and, particularly, solid solutions, have been employed to promote the oral absorption of poorly water soluble active pharmaceutical ingredients (APIs), see, for example, Ford, Pharm Acta Helv, 1986, 61:69-88. Solid dispersions and solid solutions are compositions in which API is dispersed into or dissolved in a solid matrix, generally a polymer matrix. Solid solutions and solid dispersions (in which the active pharmaceutical ingredient forms a homogeneous or nearly homogeneous glass in the excipient matrix) are of particular interest in the oral delivery of poorly water soluble compounds. It is believed that these materials improve the absorption of orally administered API by improving: (i) the wetting properties of the API; (ii) causing at the point of absorption transient supersaturation of the API with respect to a lower energy (e.g. crystalline) phase API; or (iii) both effects. In general, solid solutions are believed to enable drug absorption by enhancing the dissolution rate and/or the extent to which the drug is dissolved from the matrix.

One example of a Class II drug which has been formulated as a solid solution is posaconazole, as described in International Patent Application, publication no. WO2009/129300, published Oct. 22, 2009. Such compositions of posaconazole were prepared by forming an extrudate of posaconazole in hydroxypropylmethylcellulose acetate-succinate-derivatized polymer (HPMC-AS), which solid dispersion was subsequently blended with microcrystalline cellulose, additional HPMC-AS, hydroxypropylcellulose, and magnesium sterate. This admixture was tableted to provide an orally bioavailable posaconazole formulation with desirable PK and bioavailability.

Another example of polymers employed in providing a solid solution of polymer and API is reported by Goertz et al. in U.S. Pat. No. 4,801,460 describes solid dispersions comprising a poorly soluble drug (exemplified by theophylline) and cross-linked polyvinylpyrrolidone/vinyl acetate copolymer (PVP copolymer). The '460 patent reports drug release times of up to 8 hours in tests, and does not discuss instant release medicaments employing such polymer matrix solid solutions.

In another example, in published international application publication no. WO98/029137 (the '137 publication), published Jul. 9, 1998, Takagi et al. describes compositions comprising an API dissolved in a matrix comprising a cellulosic polymer, for example, hydroxypropylmethyl-, hydroxyethyl- and hydroxypropyl-cellulose, and salts having an endothermic heat of dissolution, for example, sodium bicarbonate, which is said to improve the rate of disintegration. The '137 publication identifies the compositions taught therein as being similar to admixtures employing a carbonate or bicarbonate salt in the presence of a solid, water soluble acid which aids disintegration when exposed to an aqueous environment via effervescent action.

In another example, Fry et al. describe formulations of HER-2 inhibitors dispersed in a wide variety of polymer matricies, including many different derivatives of cellulosic polymers (including graft copolymers incorporating cellulosic moieties), polyvinyl alcohol polymers and polyvinylpyrrolidine polymers. See published international application publication no. WO2013/056108, published Apr. 18, 2013. Such compositions are said to reduce interpatient PK variability.

Despite their growing use, the design of solid solution formulations to effectively promote oral drug absorption remains largely a matter of trial and error. Successful formulation of lipophilic compounds as solid dispersions to promote oral absorption may benefit from a strong interaction between API and polymer. This has led to interest in partially water soluble polymers with amphiphilic properties like hydroxypropyl methylcellulose acetate succinate (HPMCAS), especially when the process used to create the solid dispersion is spray drying. See Friesen et al., Mol. Pharm., 2008, 5:1003-1019. While this approach was successful for many drug candidates, it was suggested that compounds with high melting points (or high ratios of melting point to glass transition temperature) and/or particularly lipophilic compounds (e.g., those with high log P values) are especially problematic to successfully formulate as solid solutions. Friesen et al. suggests that successful formulations of compounds having high melting point properties will likely be limited to relatively dilute concentrations of API in the solid dispersion.

As will be appreciated from the foregoing, while it is desirable to provide compounds of Formula I in the form of a solid for oral dosing administered via the GI tract, of necessity the nature of the therapy provided requires that the medicament make the compound of Formula I immediately available to the patient to whom it is being administered. There is a paucity of immediate release formulations reported at the present time based on solid dispersions or solutions of a class II API in a polymer matrix.

SUMMARY OF THE INVENTION

In one aspect the present invention provides a tablet comprising:
(a) an extrudate comprising:
 (i) a water-soluble polymer matrix;
 (ii) a dispersing agent; and
 (iii) a compound of Formula I, or a pharmaceutically acceptable salt thereof:

Formula I wherein "$R^a$" is independently —H or —F, and wherein the dispersing agent and compound of Formula I is dispersed within said polymer matrix; and
(b) a disintegration system,
wherein said tablet has a hardness of from about 12 kP to about 18 kP, and wherein said tablet achieves complete disintegration in less than about 5 minutes in a standard tablet disintegration test complying with USP 31-NF26 Chapt. 701 using aqueous HCl (pH 1.8) at 37° C.

In some embodiments it is preferred for the water soluble polymer matrix of said extrudate to be a polyvinylpyrrolidone/vinyl acetate copolymer (PVP-VA) matrix.

In some embodiments it is preferred for the disintegration system to comprise powdered sodium chloride and croscarmellose sodium, and more preferably in a 1:1 wt. ratio.

In some embodiments it is preferred for a tablet to have a hardness of from about 12 kP to about 16 kP. In some embodiments it is preferred for the tablet to have a tensile strength of about 1.75 MPa.

In some embodiments it is preferred for a tablet of the invention to release at least about 90 wt % of the compound of Formula I contained therein when subjected to a dissolution test complying with USP 30 NF25 Chapt. 711, apparatus #2 equipped with USP 2 paddles, operated at 50 rpm, in 900 ml of simulated gastric fluid (pH 1.8) at 37° C.

In some embodiments, preferably the tablet comprises a disintegration system comprising:
(a) Powdered Sodium Chloride, wherein said sodium chloride is characterized by: (i) a $d_{50}$ value of less than about 210 microns; (ii) a $d_{10}$ value of less than about 50 microns; and (iii) a $d_{90}$ value of less than about 470 microns; and
(b) croscarmellose sodium,
wherein said Powdered Sodium Chloride and said croscarmellose sodium are present in a 1:1 weight ratio, and wherein the amount of extrudate present in the tablet is selected to provide from about 9 wt. % to about 10 wt. % of the compound of Formula I dispersed therein.

In some embodiments it is preferred for the disintegration system to comprise about 20 wt. % of the tablet. In some embodiments the tablet comprises about 50 wt. % extrudate In some embodiments, the tableting formulation of the invention comprises (i) the extrudate; (ii) the disintegration system; (iii) one or more diluents, in some embodiments it is preferred to select mannitol and microcrystalline cellulose as diluents; (iv) a glidant, in some embodiments it is preferred to use colloidal silica as a glidant; and (v), and one or more lubricants, in some embodiments it is preferred to use sodium stearyl fumarate as a lubricant.

In some embodiments it is preferred for the compound of Formula I to be a compound of Formula Ia, or a salt thereof:

Formula Ia wherein, each of "$R^b$" is —H or each of "$R^b$" is —F.

In some embodiments, preferably the water-soluble polymer matrix of said extrudate is a water-soluble polyvinylpyrolidone/vinyl acetate copolymer, preferably a polyvinylpyrolidone/vinyl acetate copolymer made by free-radical polymerization of a 6:4 ratio of vinylpyrrolidone:vinyl acetate monomer.

In some embodiments where the compound of Formula I is a compound of Formula Ia, preferably, the compound of Formula Ia is present in the extrudate from about 20 wt % of the extrudated to about 22 wt. % of the extrudate.

In some embodiments, preferably the extrudate comprises—tocepherol-polyethylene-glycolsuccinate (TPGS) as a dispersing agent, which is present in an amount comprising at least about 5 wt. % of the finished extrudate.

In some embodiments, preferably the extrudate comprises soluble polyvinylpyrolidone/vinyl acetate copolymer which is present in an amount comprising from about 50 wt. % of the extrudate to about 80 wt. % of the extrudate, preferably about 70 wt. % of the extrudate to about 75 wt. % of the extrudate.

In one aspect the invention provides a formulation suitable for providing a pressed tablet, the formulation comprising:
a) an extrudate composition comprising a water-soluble polyvinylpyrolidone/vinyl acetate copolymer (PVP-VA copolymer) matrix and dispersed therein:
(i) an active compound of Formula Ia, or a pharmaceutically acceptable salt thereof:

Formula Ia wherein all of $R^b$ are either —H or all of $R^b$ are —F; and
(ii) tocepherol polyethylene glycol succinate (TPGS), wherein said compound of Formula Ia comprises from about 5 wt % to about 23 wt. % of said extrudate and TPGS comprises at least about 5 wt. % of said extrudate; and
b) a disintegration system comprising: (i) croscarmellose sodium; and (ii) Powdered Sodium Chloride, wherein said disintegration system comprises about 20 wt. % of said formulation, and wherein said formulation is further characterized by providing a tablet having a hardness of from about 12 kP to about 18 kP, preferably about 12 kP to about 16 kP, which tablet when subjected to a dissolution test complying with USP 30 NF25 Chapt. 711, in a paddle-stirring apparatus equipped with USP 2 paddles, operated at 50 rpm, in 900 ml of simulated gastric fluid (pH 1.8) at 37° C. releases at least about 90% of the compound of Formula Ia contained therein in less than about 20 minutes.

In some embodiments a tablet formulation of the invention comprises in addition to extrudate and disintegration system: (i) mannitol, preferably about 20 wt. % of the formulation; (ii) microcrystalline cellulose, preferably up to about 20 wt. % of the formulation; (iii) colloidal silica, preferably about 0.25 wt. % of the formulation; and (iv) sodium stearyl fumarate, preferably about 0.75 wt. % of the formulation. In some embodiments, preferably the tablet formulation comprises about 50 wt. % of said extrudate.

DETAILED DESCRIPTION OF THE INVENTION

The following terminology, which may be used herein, is used in accordance with the following definitions.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between.

The term "formulation", as used herein, refers to a blend, aggregation, solution or other combination of materials which includes an active pharmaceutical ingredient (API) which formulation is adapted to a particular mode of administration, for example, a formulation suitable for pressing into tablets designed for oral administration, in the treatment, management, prevention and etc. of a disease state or condition in a patient.

The term "subject" as used herein refers to an animal, preferably a mammal, most preferably a human, who has been the object of treatment, observation or experiment. When a human subject suffering from the condition to be treated is included in the activity they are alternatively referred to herein as a "patient".

As mentioned above, the present invention is directed to an extruded composition (extrudate) comprising a soluble polymer matrix and dispersed or dissolved therein a compound of Formula I, or a pharmaceutically acceptable salt thereof:

Formula I wherein "R$^a$" is independently —H or —F, and a dispersing agent, for example, vitamin E polyethylene glycol succinate (TPGS), which extrudate is incorporated into a pharmaceutical formulation comprising a disintegration system, which formulation is suitable for providing tablets of up to 18 kP, in some embodiments, preferably 16 kP, hardness which disintegrate within about 5 minutes in standard disintegration tests.

Compound of Formula I suitable for use in compositions of the invention may be prepared in accordance with the synthesis described in WO 2012/064910. In some embodiments it is preferable to crystallize the crude compound of Formula I prepared in accordance with the foregoing from an ethanol/water solvent, thus providing a crystalline trihydrate form of the compound, and to mill the crystalline material to a particle size that provides a free-flowing powder which can be fed into the extruder equipment used in preparing the dispersion. As will be appreciated, where noted, weights and weight percentage relationships described for the compound of Formula I in formulations and tablets described herein are adjusted to reflect the weight of an equivalent amount of 100% active free-base of the compound without solvent of crystallization or inert material as would be taken into consideration when preparing the formulation using materials having less than 100% activity.

Figure 1:
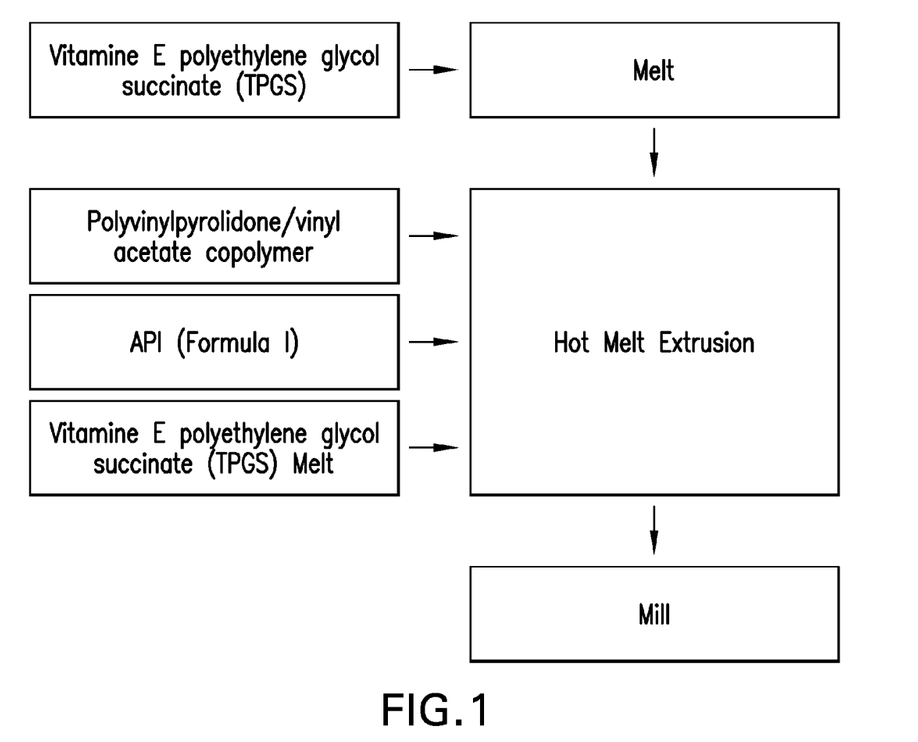
FIG. 1: Flow Chart Illustrating Unit Operations in General Preparation of Dispersion of the Invention
Figure 2:
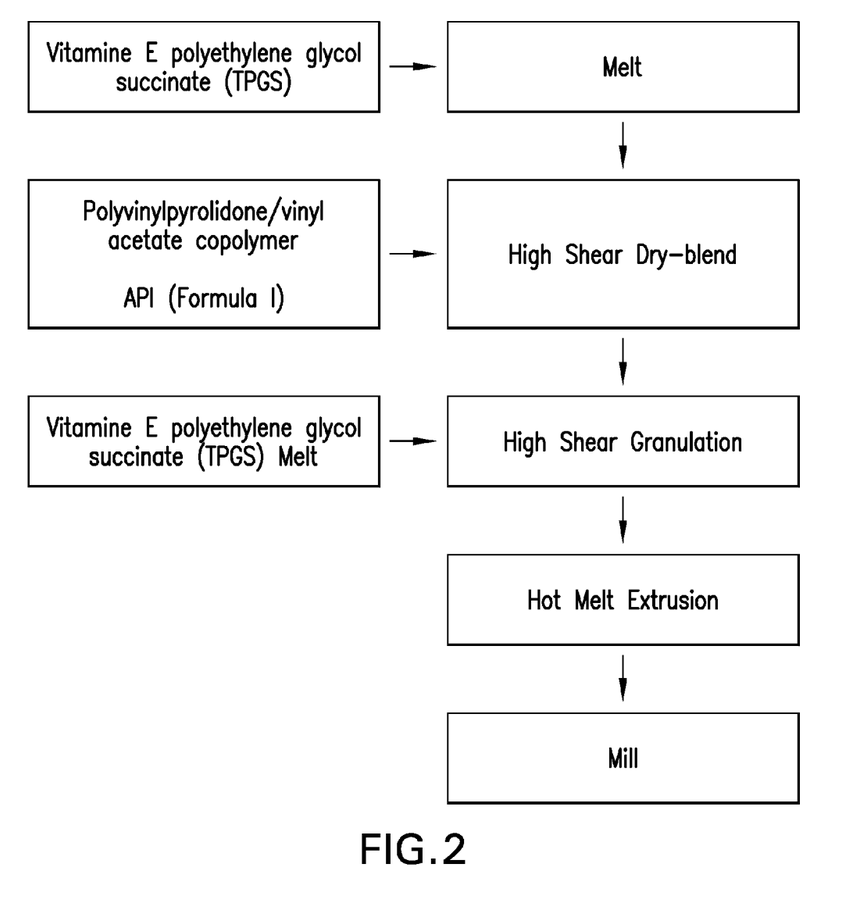
FIG. 2: Flow Chart Illustrating Unit Operations in Alternative General Preparation of Dispersion of the Invention

With reference to FIGS. 1 and 2, in general the extrudate is prepared by hot-melt extrusion (HME) of a compound of Formula I and various excipients which may or may not have received additional operations to render them suitable for HME processing.

The inventors have surprisingly found that, contrary to common experience with Class II pharmaceutical compounds which are frequently dispersed in many different polymers, as discussed above, the compounds of Formula I tend to thermally degrade when attempts are made to incorporate them into a matrix comprising certain commercially available cellulosic polymers using HME techniques. For example, using HPMCAS as the polymer matrix leads to the formation of excessive degradation products in the dispersion produced. In some experiments, use of a cellulosic polymer as the dispersion matrix for preparing dispersions of the compound of Formula I by HME resulted in up to 25 times the amount of API degradation that subjecting the API alone to the same thermal excursion generated.

Surprisingly, the inventors have found that one type of commercially available polymer material from which a dispersion of the compound of Formula I could be prepared without exacerbating thermal degradation of the compound was the commercially available water-soluble polymers, for example, polyvinylpyrrolidone/vinylacetate copolymers (PVP-VA polymers). It was surprisingly found that dispersions prepared by HME technique using a water-soluble polymer, for example a PVP-VA polymer and a compound of Formula I resulted in no greater thermal degradation than subjecting the raw compound of Formula I alone to the same thermal excursion. Accordingly, intimate mixtures of free base compound "FIa-H" (the compound of Formula Ia wherein all of "R$^b$" are —H,) or of the free base compound "FIa-F" (the compound of Formula Ia wherein all of "R$^b$" are —F) and one of two potential matrix polymers were subjected to 2 minutes of heating to 170° C. on a TGA instrument stage, then cooled to room temperature and evaluated spectroscopically for the formation of known thermal degradation products. These data is summarized in Table I.

TABLE I

| Composition | Initial mole % degradation products present | 170° C., 2 min. Mole % degradation products present |
|---|---|---|
| FIa-H alone (crystalline material) | 0.18 | 0.18 |
| FIa-H alone (amorphous material) | 0.11 | 0.11 |
| FIa-F alone (amorphous material) | 0.11 | 0.11 |
| FIa-H + PVP-VA | 0.42 | 0.77 |
| FIa-H + HPMCAS | 0.15 | 3.57 |
| FIa-F + PVP-VA | 0.10 | 0.15 |
| FIa-F + HPMCAS | 0.08 | 2.25 |

As illustrated in Table I, these data indicate that some commercially available cellulosic polymers exacerbate thermal degradation of both the FIa-H compound and the FIa-F compound. Moreover, the inventors have found that typically HME processing temperatures can reach 180° C., which results in even greater percentage of loss of a compound of Formula I to degradation products. Thus, the investigators surprisingly found that dispersing compounds of Formula I in soluble copolymers of polyvinylpyrrolidone/vinyl acetate copolymer (PVP-VA copolymer) using a hot-melt extrusion (HME) processing technique run with the same thermal excursions used when a cellulosic polymer was employed resulted in a reduction of degradation products detected in the extrudate product. Typically, the percentage increase of degradation product observed in such extrudate was no greater than the percentage of degradation product observed when samples of the same compound of Formula I was subjected to the same thermal excursion experienced in the HME process.

In accordance with the foregoing, suitable water-soluble polymers for use in compositions of the invention are any soluble PVP-VA copolymer which is made by free-radical polymerization of a 6:4 ratio of vinylpyrrolidone:vinyl acetate monomer. An example of commercially available copolymer of this type is the polyvinylpyrrolidone/vinylacetate copolymer sold under the trade name Kollidon® 64, and equivalents thereof.

In addition to a matrix polymer and at least one compound of Formula I, an extrudate of the invention will include some amount of an excipient which acts as a dispersing agent. As the term is used herein a dispersing agent can reduce the thermal energy required to drive compound of Formula I into solution in the matrix polymer and promote formation of the dispersion with even lower degradation losses in the compound of Formula I dispersed in the matrix. For extrudates of the invention, in some embodiments it is preferred to employ vitamin E in the form of its polyethylene glycol succinate (d-alpha-tocopheryl polyethyleneglycol succinate, or TPGS, herein). An example of a commercially available TPGS suitable for use in extrudates of the invention are any that provide esterified d-alpha-tocopheryl succinate with polyethylene glycol 1000, for example, but not limited to, Vitamin E d-TPGS NF from Eastman Chemical Company. In some embodiments, preferably TPGS is used as the dispersing agent and is present in the finished extrudate in an amount that is at least about 5 wt. % of the extruded composition.

It will be appreciated that other dispersing agents, for example, polyethoxylated castor oil (for example, cremophor) may also be employed.

The relative amount of the compound of Formula I, matrix polymer and dispersing agent employed in compositions of the invention, expressed as a wt. % of the extruded composition (extrudate), can vary and still be within the scope of the invention. Typically, the matrix polymer is present in an amount making up the balance of the composition after subtracting the wt. % of the API and dispersing agent. Typically the amount of matrix polymer is from about 70 wt. % to 75 wt. % of the finished extrudate. In some embodiments compositions of the invention are preferred that include an amount of the compound of Formula I which, corrected for its relative activity in comparison to 100% pure freebase compound of Formula I, is equivalent to no more than 25 wt. % of 100% free-base compound contained within the finished extrudate composition. In some embodiments, preferably the amount of the compound of Formula I present in the finished extrudate is equivalent in activity to from about 5 wt. % to about 22 wt. % of 100% pure free-base compound in the finished extrudate, and more preferably an amount equivalent in activity to at least about 20 wt. % of the 100% free base compound in the finished extrudate.

Compositions of the invention may be prepared by processes that are suitable for causing the selected API (for example, a compound of Formula Ia) to form a dispersion throughout the polymer matrix such that the drug is generally an amorphous uniform dispersion in the polymer or dissolved in the polymer. In general this requires some method of heating and mixing the constituents of the desired composition together and recovering the dispersion or solution in a solid form. Although it will be appreciated that any means affording a dispersion may be employed without departing from the invention, in some embodiments it is preferred to prepare compositions of the invention via Hot Melt Extrusion (HME). Hot melt extrusion (HME) is a technique in which an extruder, for example, a 27 mm Leistritz twin screw extruder, is employed to blend and heat the polymer, drug, and dispersing agent, whilst forming the finished composition dispersion or solution into a "noodle" or other conveniently handled shape which may be employed in further processing in the preparation of tableting formulations (extrudate).

In carrying out such operations, some or all of the components may be premixed prior to introducing them into the extruder, for example, by blending dry powders or wet milling or wet mixing, the constituents together in a blending, mixing or granulation process to insure intimately mixed constituents that lead to a homogeneous blend of constituents when the blend is fed into the extruder. Alternatively, the constituents may be fed into the extruder using independent feed streams (see Polymer Extrusion $4^{th}$ Edition by Chris Rauwendaal 2001, Hanser Gardner Publications, Inc., Cincinnati, Ohio or Schenck et al., (2010), Achieving a Hot Melt Extrusion Design Space for the Production of Solid Solutions, in Chemical Engineering in the Pharmaceutical Industry: R&D to Manufacturing (ed. D. J. am Ende), John Wiley & Sons, Inc., Hoboken, N.J., USA). Although for some compositions of the invention it is preferred to employ an HME process to prepare them, it will be appreciated that compositions of the invention can be prepared by any means useful for preparing a melt in any convenient apparatus in which an admixture of a compound of Formula I, matrix polymer and dispersing agent can be heated, mixed, and recovered.

In general, when extruding materials, the act of transporting the material through the extruder results in imparting energy to the material, which is converted to heat in the transported material. When heat transfer from the extruder power consumed in material transport is not by itself sufficient to achieve the temperature required to produce the desired dispersion or solution of a compound of Formula I in the polymer matrix, generally the barrel of the extruder is provided with means to impart additional heat to the material. In like manner, different sections of the extruder barrel can be heated or cooled, as needed, to maintain a particular temperature within a section of the extruder barrel or even extract heat in a different section of the extruder barrel to cool the material as it is passing through. In general the extruder temperature, power and transport speed of the extruder are set to provide the minimum temperature excursion and residence time needed to insure that a homogeneous dispersion or solution is prepared, thus minimizing the amount of API that undergoes degradation during processing.

In general, the extrudate emerging from an extruder is in a plastic state and solidifies upon emerging from the barrel due to pressure release and cooling. During this transition, typically the extrudate has a profile shape, for example, noodles, bars, cylinders, etc., and is "cut" into convenient length pieces. Once extrudate pieces are obtained, they can be further mechanically processed to provide a convenient form for incorporation into a dosage form, for example, by milling, grinding, or sieving. As the term is used herein, the material emerging from the extruder, and any form into which that material is subsequently rendered by mechanical processes, for example, milling, grinding, blending, sieving or granulating, is termed the "extrudate". Exemplary extruders include those provided by Leistritz, for example a 27 mm Leistritz twin screw extruder, and those provided by Thermo-Fisher, for example, a 16 mm twin screw Thermo-Fisher extruder. This equipment is generally equipped with means of heating the extruder barrel permitting it to be used in a "hot melt extrusion" operation.

Once the extrudate is rendered into a convenient form for further processing, it can be incorporated into a formulation for use in providing a dosage form suitable for oral administration, for example, a formulation adapted for pressing into tablets or filling into capsules. To achieve the dissolution and disintegration targets needed for effectively administering a compound of Formula I in the provision of migraine therapy, a formulation is prepared which comprises the finished extrudate, preferably milled to provide a powdered form that is easily blended with the other constituents of the formulation, a disintegration system and other excipients, for example diluent and lubricant, useful in preparing a formulation suitable for tableting. For use in a formulation of the present invention, the disintegration system comprises a conventional disintegrant, for example, croscarmellose sodium or crospovidone, and Powdered Sodium Chloride, where "Powdered Sodium Chloride" has the meaning presented herein.

For use in a disintegration system of the present invention, the phrase "Powdered Sodium Chloride" means sodium chloride which has been processed to a form having a particle distribution which yields the following values: (i) $d_{50}$ of less than about 210 microns, for example, about 195 microns; (ii) $d_{10}$ of less than about 50 microns, for example, between 43 microns and 44 microns; (iii) a $d_{90}$ of less than about 470 microns, for example, about 460 microns, and wherein the material displays a volume mean diameter of less than about 240 microns, for example, about 230 microns. An example of one such type of sodium chloride which is commercially available is provided by Avantor™ under the product designation "Sodium Chloride, Powder, USP GenAR® product no. 7540".

The data shown in Table II illustrate the need to employ Powdered Sodium Chloride in the disintegration system in formulations of the invention. Accordingly, test tablets comprising an extrudate of the invention (said extrudate comprising PVP-VA matrix, a compound of Formula Ia (FIa-H), and TPGS), a diluent comprising microcrystalline cellulose and a disintegration system consisting of crosscarmellose sodium and the salt shown in the left-hand column of Table II were subjected to a disintegration test complying with USP 31-NF26 Chapt. 701 in a standard disintegration testing apparatus (Pharamatron DT50) using aqueous HCl (pH 1.8) as a disintegration medium at 37° C. As reflected in Table II, surprisingly, only the tablet employing the Powdered Sodium Chloride in the disintegration system was able to meet the dissintegration target of less than 5 minutes (tablet compression force controlled to provide tablets of consistent hardness and thickness for all formulations).

TABLE II

| Salt in Disintegration System | Disintegration time, aqueous HCl (pH 1.8) |
| --- | --- |
| None | Greater than 1 hour |
| Powdered Sodium Chloride | 1.5 minutes |
| Granular potassium carbonate | 6 minutes |
| Granular sodium chloride | 18 minutes |
| Granular sodium carbonate | 13 minutes |
| Powdered sodium bicarbonate | 17 minutes |
| Powdered sodium sulfate | 20 minutes |
| Granular sodium phosphate (dibasic) | 22 minutes |

Moreover, when equivalent tablets were made using Powdered Sodium Chloride alone, without croscarmellose sodium, it was found that tablet disintegration times exceeded 5 minutes as well. Accordingly, in some embodiments it is preferable that the disintegration system comprise a conventional disintegrant in conjunction with Powdered Sodium Chloride, and more preferably in a weight ratio of 1:1, Powdered Sodium Chloride:Disintegrant. Without being bound by theory, it is believed that the Powdered Sodium Chloride exhibits dissolution kinetics that are rapid compared with the rate of gelation of the polymer matrix when a tablet of the invention is exposed to the intended dissolution environment (human GI tract). Again without being bound by theory, the Powdered Sodium Chloride is believed by virtue of its particulate profile to have a combination of desirable dissolution kinetics and ability to form with sufficient rapidity (more rapidly than the rate of gelation of the matrix polymer) a local boundary layer of sufficient ionic strength to suppress gel-formation in the matrix polymer, and thereby to facilitate release of a compound of Formula I from the tableted formulation, which would otherwise be inhibited by gel formation in the matrix polymer. It will be appreciated that other salts if provided in a form which displays the same combination of rapid dissolution kinetics and the ability to rapidly form a local boundary layer of sufficient ionic strength to suppress gelation can also be employed in a formulation of the invention without departing from the scope of the invention defined herein.

In formulations of the invention, a suitable disintegrant for use in disintegration systems of the invention is, for example, croscarmellose sodium (crosslinked sodium carboxymethylcellulose polymer), for example, the AC-Di-Sol® line of polymers available from FMC. It will be appreciated that other disintegrants may be employed to provide an effective disintegration system, for example, crospovidone, if they are used in accordance with the other aspects of the disintegration system described herein and not depart from the scope of the invention.

The compounds of Formula I are directed to treatment of migraine, and as such, a rapid-release formulation is thought to be important in providing a therapeutic benefit to human patients to whom such a tablet is administered.

As is known, two qualities of tablet and capsule dosage forms important to release of an active pharmaceutical compound therefrom may be demonstrated using standard tests to measure the disintegration time and/or the dissolution time of the dosage form. A disintegration test measures the amount of time required for the dosage form to visibly disintegrate and wash out of a standard basket contained in a standard apparatus under standard operating conditions. A standard disintegration test is described for tablets and capsules in USP 31-NF26, Chapt. 701, beginning at p 266. There are equivalents thereto described in, for example, the European Pharmacopoeia and the Japanese Pharmacopoeia, which standard tests are generally accepted in the regulatory bodies of most countries. As the term is used herein with reference to formulations and tablets of the invention, "disintegration time" means: as determined in accordance with a test complying with this standard run at 37° C. using aqueous HCl (pH 1.8) as a disintegration fluid.

Dosage forms intended for oral administration may also be measured in a dissolution test, wherein the time-rate release of an amount of therapeutic compound dissolved into a standard media in a standard apparatus is measured after introducing the dosage form into the testing medium. A standard dissolution test for tablets and capsules is described in, for example, USP 36, chapt 711. Equivalent tests are described in the European Pharmacopoeia and the Japanese Pharmacopoeia, and in guidance from the US FDA, for example, in "*Guidance for Industry, Dissolution Testing of Immediate Release Solid Oral Dosage Forms*" published August, 1997 by the U.S. Department of Health and Human Services, Food and Drug Administration, Center for Drug Evaluation and Research, pp 1-13 and references therein. As the term is used herein with reference to formulations and tablets of the invention, "disintegration time" means: as determined in accordance with a test complying with this standard in a standard dissolution apparatus equipped with USP 2 paddles, operated at 50 rpm, in 900 ml of simulated gastric fluid (pH 1.8) at 37° C.]

In one aspect the invention provides a formulation adapted to preparing tablets comprising an extrudate of the invention, a disintegration system comprising Powdered Sodium Chloride and croscarmellose sodium, and other excipients, for example, diluents, glidants and lubricants, in amounts that, once the formulation is pressed into a table having a hardness of from about 12 kP to about 16 kP, and in some embodiments, 12 kP to about 18 kP, provides a tablet releasing more than 90% of the API contained therein in less than about 20 minutes when subjected to dissolution testing in a standard dissolution apparatus equipped with USP 2 paddles, operated at 50 rpm, in 900 ml of simulated gastric fluid (pH 1.8) at 37° C., in accordance with the procedures outlined in "*Guidance for Industry, Dissolution Testing of Immediate Release Solid Oral Dosage Forms*" published August, 1997 by the U.S. Department of Health and Human Services, Food and Drug Administration, Center for Drug Evaluation and Research, pp 1-13 and references therein where the tablet hardness exceeds.

Where tablet hardness is used herein, it is in reference to a tablet having a 500 mg target weight and a caplet shape or a 652.2 mg target weight in a caplet shape. Accordingly, as the term is used herein, tablets having a hardness in the range of 12 kPa to 16 kPa have a corresponding tensile strength of about 1.75 MPa, and tablets having a hardness in the range of 19 kPa to 22 kPa have a tensile strength of about 2.75 Mpa.

Formulations of the invention used in preparation of oral dosage forms (i.e., tablets or capsules) may further comprise other excipients. For example: a typical formulation of the invention directed to the preparation of a pressed tablet may contain a diluent (for example, mannitol, article of commerce, and/or microcrystalline cellulose, for example Avicel®); a glidant (for example, colloidal silica, for example Cab-O-Sil®); and a lubricant (for example, sodium stearyl fumarate, article of commerce). It will be appreciated that in formulating compositions of the invention, other diluents, glidants, and lubricants may be substituted to effect similar formulations.

The following definitions apply to excipients which may be used in formulations of the invention as the terms are used herein:

a diluent is an excipient which increase the bulk of a dosage form, typically where the active pharmaceutical ingredient in the formulation is too potent to permit convenient processing or administration of a dosage form which does not include a diluent, or where the formulation by itself without a diluent makes formation of the dosage form difficult (for example, where an aliquot of the formulation without a diluent would be of too small of a volume to form the aliquot into a tablet);

a disintegrant is an excipient that expands and/or dissolves when placed in an aqueous environment, for example, the gastrointestinal tract, which aids a tablet in breaking apart and promotes release of an active pharmaceutical ingredient contained in a tablet;

a "disintegration system" is a combination of a conventional disintegrant and a rapidly dissolving salt which provides beneficial antigellation effects when placed into an environment in which the dosage form within which the disintegration system is incorporated is placed into an environment in which the dosage form disintegrates, for example, simulate gastric fluid, the gastrointestinal tract of a subject or aqueous HCl at pH 1.8;

a Glidant is an excipient, for example colloidal silica, that enhances the flow of a granular mixture by reducing inter-particle friction.

Pharmaceutical formulations intended for the preparation of oral dosage forms (tablets and capsules) may further contain one or more agents selected from the group consisting of sweetening agents, flavoring agents, coloring agents and preserving agents in order to provide pharmaceutically elegant and palatable preparations.

The preparation of formulations of the invention suitable for use in providing solid oral dosage forms comprising a composition of the invention may involve blending, roller compaction or wet granulation to densify and/or reduce the risk of segregation of components during subsequent handling (e.g., compression into tablets). Granulation steps can also be used to minimize the impact of raw material property variability (e.g., excipient particle size) on subsequent processing (e.g., tablet compression) and ultimate product performance. Lubrication is typically performed prior to roller compaction and tablet compression to reduce the tendency of material to adhere to compression surfaces (e.g., tablet tooling). In general lubricants are derivatives of stearic acid, for example, magnesium stearate or sodium stearly fumarate. Techniques and methods useful in preparation of dosage forms are know, for example, as described in Ansel, Introduction to Pharmaceutical Dosage Forms, Seventh Edition, 1999.

In general, preparation of oral dosage forms from pharmaceutical formulations of the invention requires that the pharmaceutical formulation of the invention (admixture of excipients, disintegrating system and composition of the invention) is compressed into a tablet or charged into a capsules. Tablets can be prepared with a variety of possible shapes (ellipsoidal, capsule, biconvex round, etc.). The powder can also be encapsulated in capsule dosage (e.g., using hard gelatin capsules). Techniques suitable for preparing solid oral dosage forms of the present invention are described in Remington's Pharmaceutical Sciences, 18th edition, edited by A. R. Gennaro, 1990, Chapter 89 and in Remington—The Science and Practice of Pharmacy, 21st edition, 2005, Chapter 45. In some embodiments of the present invention, it is preferred to prepare a tablet having a hardness of 16 kP or less, where the tablet has a target of providing the equivalent of 50 mg of a compound of Formula Ia (100% freebase), by placing 462.5 to 537.5 mg of the formulation into tableting tooling having an Elizabeth Carbide Die Company™ drawing number P-14305-B and pressing it in a Korsch™ tableting press.

Figure 3:
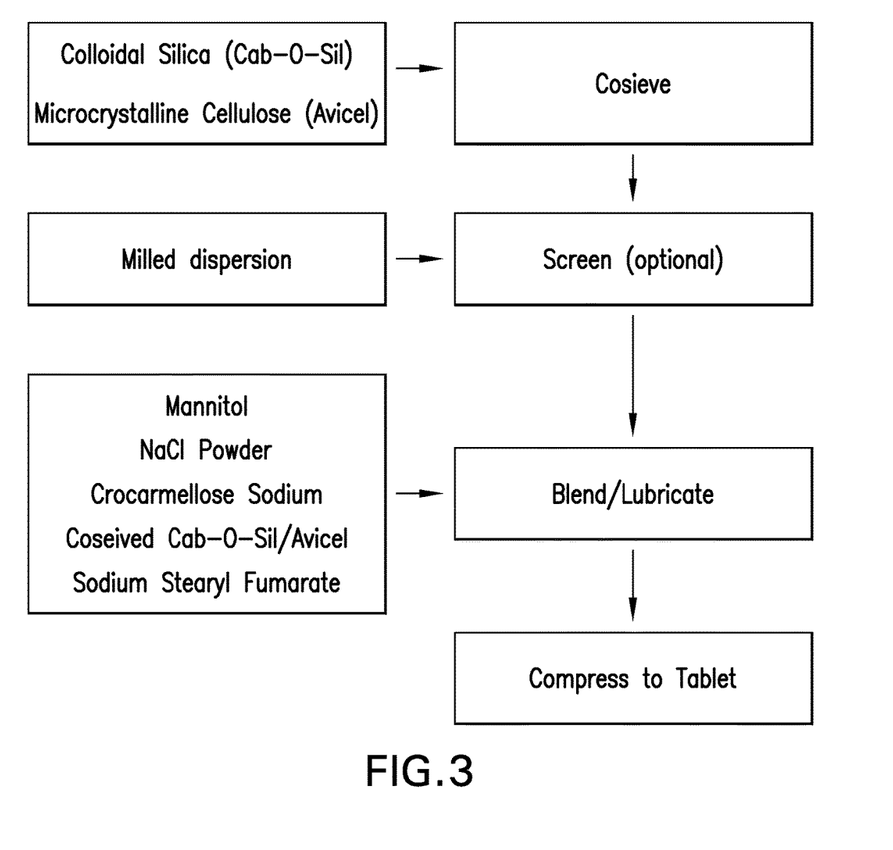
FIG. 3: Flow Chart Illustrating Unit Operations in Formulating Tablets of the Invention

With reference to FIG. 3, in general, compositions of the invention are prepared by dry-blending various excipients with milled dispersion (soluble polymer matrix comprising API dispersed therein), and compressing the blend to tablets.

What follows is a description of the general procedures employed in preparing the extrudate, preparing a tableting formulation comprising the extrudate and preparing tablets of the invention therefrom. The following examples serve only to illustrate the invention and its practice. The examples are not to be construed as limitations on the scope or spirit of the invention.

Example I—Preparation of a Extrudate Comprising Kollidon® 64, TPGS and (S)—N-((3S,5S,6R)-6-methyl-2-oxo-5-phenyl-1-(2,2,2-trifluoroethyl)piperidin-3-yl)-2'-oxo-1',2',5,7-tetrahydrospiro[cyclopenta[b]pyridine-6,3'-pyrrolo[2,3-b]pyridine]-3-carboxamide (FIa-H), a Tableting Formulation and Tablets Prepared Therefrom With reference to FIG. 2, extrudate comprising a water-soluble polymer matrix and dispersed therein API was prepared by:

(i) forming FIa-H/Matrix polymer pre-mix by dry-blending an amount of crystalline FIa-H and polyvinylpyrolidone/vinyl acetate copolymer (Matrix polymer) to provide a pre-mix having a weight ratio of API:Matrix polymer of 1:3.75;

(ii) feeding an amount of the API/Matrix pre-mix and an amount of molten alpha-tocopherol/propylene glycol succinate (TPGS) to provide a weight ratio of 19:1, API premix:TPGS into the extruder; and (iii) maintaining the extruder apparatus at a barrel temperature, feed rate and screw speed that provides an extrudate comprising a solid solution of the API in a matrix (polyvinylpyrolidone-vinylacetate copolymer/TPGS) comprising about 20 wt % of the active API.

Accordingly, 1.318 Kg of FIa-H (compound of Formula Ia wherein all "$R^b$" are —H) trihydrate was blended with 4.382 Kg of matrix polymer. TPGS (0.300 Kg) was melted and added to the blend of FIa-H and VA-64 in a high shear granulator. Blended API, VA-64, and TPGS was prepared in eight separate blending runs using a Diosna high shear granulator with a 6 L bowl, an impeller speed of 1000 rpm, a chopper speed of (600) rpm. In each run the blender was operated form 1 minute to mix FIa-H and the matrix polymer, then melted TPGS was added via pipette over 5 minutes of time maintaining the impeller and chopper speeds. After TPGS addition, the blend was mixed for an additional 1 minute maintaining the impeller and chopper speed.

The blend material was fed into a Thermo-Fischer 16 mm extruder while maintaining a product temperature of from about 146° C. to about 160° C., die pressure from about 14 bar to about 16 bar, a powder feed rate from 30-52 g/min., to provide 6.0 Kg of an extrudate of the invention. This material was milled in a Fitzmill equipped with screen size 0 (0.027") and using the following operating conditions: an impeller speed of 2000-4500 prm, and impact: forward blade direction. The milled extrudate material was sized by passing it through a 600 micron screen providing a powder (extrudate intermediate) having a VMD of approx 195 microns when measured by QICPIC for use in preparing a blend for pressing into tablets (tableting blend).

A tableting blend (6 kg) was prepared using 3.6 kg of extrudate intermediate comprising the equivalent of 200 mg/g of 100% freebase FIa-H, 1.160 kg of mannitol SD 10, 0.600 kg of sodium chloride powder, 0.600 kg of cross carmellose sodium, 0.01500 kg of colloidal silica, 0.09000 kg of sodium stearyl fumarate, and 0.5798 kg of Avicel PH102. The blender speed was 25 rpm and the blender time was 5 minutes.

The tableting blend was sub-divided to 1.250 kg sub-parts and tablets corresponding to hardness ranges of 12-16 kP, 19-22 kP, and 24-28 kP were prepared by compressing aliquots from each portion of the tableting blend on a Korsch X1100 equipped with upper and lower tools with face drawing P14305-B, that is a plain oval tool measuring 14.68 mm×8.33 mm.

Tablets having a hardness in the range of 12 kP to 16 kP were tested in accordance with a test complying with USP 30 NF25 Chapt. 711, paddle stirrer apparatus equipped with USP 2 paddles, operated at 50 rpm, in 900 ml of simulated gastric fluid (pH 1.8) at 37° C., these tablets met the release profile goal of 90% FIa-F contained in the tablet dissolved in less than 20 minutes.

Example II—Preparation of a Extrudate Comprising Kollidon® 64, TPGS and (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide) (FIa-F)), a Tableting Formulation and Tablets Prepared Therefrom Using the general preparation shown in Example I, 1.421 Kg of FIa-F (compound of Formula Ia wherein all "R$^b$" are —F) was blended with 4.320 Kg of matrix polymer in a 25.0 L Fielder Granulator, impeller speed set to 'fast', chopper speed set to 'high'. Into the granulator was added 0.300 Kg of TPGS over five minutes while maintaining the impeller and chopper speeds. This blended material was hot-melt extruded in a Thermo-Fisher 16 mm extruder set to provide a product temperature of 158° C., powder feed rate of 20 g/minute, and die pressure maintained at 2-4 Bar, yielding 4.52 Kg of extrudate.

The extrudate thus prepared (3.3 Kg) was milled with a Fitzmill, screen size 000 (0.20"), with impact blade set in the 'forward' direction and an impeller speed set to target 3000 rpm (2000 rpm to 6000 rpm). Milled extrudate was screened through a 600 micron screen yielding 3.01 Kg of screened extrudate. A portion of the screened material (3.0 Kg) was blended with sodium stearyl fumarate (0.05625 Kg), silicon dioxide (0.01875 Kg), microcrystalline cellulose (0.9750 Kg), Powdered Sodium Chloride (0.750 Kg) and mannitol (1.950 Kg) using a V-blender operating at 24 rpm.

Two aliquots of the tableting blend prepared above (1.957 Kg) were pressed into tablets corresponding to hardness ranges of 12 kP-18 kP and 20 kP-26 kP respectively, on a Korsch X1100 tableting press equipped with upper and lower tools with face drawing P10165-B (plain/plain) oval tool measuring 15.88 mm×8.81 mm with a tablet target weight of 652.2 mg.

Tablets were dissolved in a paddle stir dissolution apparatus using simulated gastric fluid at 37° C., paddle speed 50 rpm in a test complying with USP 30 NF25 Chapt. 711, these tablets met the release profile goal of 90% of FIa-F contained in the tablet dissolved in less than 20 minutes, and the disintegration goal of complete disintegration in less than 5 minutes when tested using a disintegration test complying with USP 31-NF26 Chapt. 701 in a standard disintegration testing apparatus (Pharamatron DT50) using aqueous HCl (pH 1.8) as a disintegration medium at 37° C. tested in aqueous HCl (pH 1.8) at 37° C.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A tablet comprising:
(a) an extrudate comprising:
(i) a water-soluble polymer matrix;
(ii) a dispersing agent; and
(iii) a compound of Formula I, or a pharmaceutically acceptable salt thereof:

Formula I wherein "R$^a$" is independently —H or —F, and wherein the dispersing agent and compound of Formula I is dispersed within said polymer matrix; and
(b) a disintegration system,
wherein said tablet has a hardness of from about 12 kP to about 18 kP, and wherein said tablet achieves complete disintegration in less than about 5 minutes in a tablet disintegration test complying with USP 31-NF26 Chapt. 701 using aqueous HCl at pH 1.8 at 37° C.

2. The tablet of claim 1 wherein the polymer matrix in said extrudate is a water soluble polyvinylpyrrolidone/vinyl acetate (PVP-VA) copolymer.

3. The tablet of claim 1 wherein said disintegration system comprises powdered sodium chloride and croscarmellose sodium.

4. The tablet of claim 1 wherein the compound of Formula I is a compound of Formula Ia, or a salt thereof:

Formula Ia wherein, each of "$R^b$" is —H or each of "$R^b$" is —F.

5. The tablet of claim 4 which further comprises: (a) mannitol; (b) colloidal silica; (c) microcrystalline cellulose; and (d) sodium stearyl fumarate.

6. The tablet of claim 1 wherein said extrudate comprises about 50 wt % of said tablet and said extrudate is comprised of from about 5 wt % to about 23 wt % of a compound of Formula I.

7. A tablet comprising:
(a) an extrudate comprising:
  (i) a polymer matrix which is a water soluble polyvinylpyrrolidone/vinyl acetate copolymer;
  (ii) a dispersing agent; and
  (iii) a compound of Formula I, or a pharmaceutically acceptable salt thereof:

Formula I wherein "IV" is independently —H or —F, and wherein the dispersing agent and compound of Formula I is dispersed within said polymer matrix; and
(b) a disintegration system comprising powdered sodium chloride and croscarmellose sodium.

8. The tablet of claim 7 wherein the disintegration system comprises a 1:1 weight ratio of powdered sodium chloride and croscarmellose sodium.

9. The tablet of claim 8 wherein the dispersing agent in said extrudate is d-alpha-tocopheryl polyethyleneglycol succinate (TPGS).

10. The tablet of claim 7 wherein the tablet has a hardness of from about 12 kP to about 18 kP, and wherein when said tablet is subjected to a dissolution test complying with USP 30 NF25 Chapt. 711, in a paddle-stirring apparatus equipped with USP 2 paddles, operated at 50 rpm, in 900 ml of simulated gastric fluid at pH 1.8 at 37° C. releases at least about 90% of the compound of Formula I contained therein in less than about 20 minutes.

11. The tablet of claim 7 wherein the tablet has a tensile strength of 1.75 MPa, and wherein when said tablet is subjected to a dissolution test complying with USP 30 NF25 Chapt. 711, in a paddle-stirring apparatus equipped with USP 2 paddles, operated at 50 rpm, in 900 ml of simulated gastric fluid at pH 1.8 at 37° C. releases at least about 90% of the compound of Formula I contained therein in less than about 20 minutes.

12. The tablet of claim 7 wherein the compound is (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide.

13. The tablet of claim 7 wherein the compound is (S)—N-((3S,5S,6R)-6-methyl-2-oxo-5-phenyl-1-(2,2,2-trifluoroethyl)piperidin-3-yl)-2'-oxo-1',2',5,7-tetrahydrospiro[cyclopenta[b]pyridine-6,3'-pyrrolo[2,3-b]pyridine]-3-carboxamide.

14. The tablet of claim 7 wherein said powdered sodium chloride has: (i) a $d_{50}$ value of less than about 210 microns; (ii) a $d_{10}$ value of less than about 50 microns; and (iii) a $d_{90}$ value of less than about 470 microns.

15. The tablet of claim 7 wherein the water-soluble polymer matrix of said extrudate is a copolymer having about a 6:4 polyvinylpyrrolidone/vinyl acetate monomer unit ratio.

16. A formulation suitable for pressing into a tablet, said formulation comprising:
a) an extrudate composition comprising a water-soluble polyvinylpyrrolidone/vinyl acetate copolymer (PVP-VA copolymer) matrix and dispersed therein:
  (i) a compound of Formula Ia, or a pharmaceutically acceptable salt thereof:

Formula Ia wherein all of $R^b$ are either —H or all of $R^b$ are —F; and
and
(ii) tocopherol polyethylene glycol succinate (TPGS), wherein said compound of Formula Ia comprises from about 5 wt % to about 23 wt % of said extrudate and TPGS comprises at least about 5 wt % of said extrudate; and b) a disintegration system comprising: (i) croscarmellose sodium; and (ii) powdered sodium chloride, wherein said disintegration system comprises about 20 wt % of said formulation.

17. The formulation of claim 16 further comprising: (a) mannitol; (b) colloidal silica; (c) microcrystalline cellulose; and (d) sodium stearyl fumarate, and wherein said powdered sodium chloride is characterized by: (i) a $d_{50}$ value of less than about 210 microns; (ii) a $d_{10}$ value of less than about 50 microns; and (iii) a $d_{90}$ value of less than about 470 microns.

18. The formulation of claim 17 wherein the weight ratio of compound of Formula Ia: powdered sodium chloride: croscarmellose sodium is 9:10:10.

19. The formulation of claim 18 wherein said compound of Formula Ia is (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide or (S)—N-((3S,5S,6R)-6-methyl-2-oxo-5-phenyl-1-(2,2,2-trifluoroethyl)piperidin-3-yl)-2'-oxo-1',2',5,7-tetrahydrospiro[cyclopenta[b]pyridine-6,3'-pyrrolo[2,3-b]pyridine]-3-carboxamide.

20. The formulation of claim 17 wherein said extrudate is present in an amount of about 50 wt % of the formulation.

21. A tablet made by pressing a formulation of claim 16 in a tableting press to provide a tablet with a tensile strength of about 1.75 MPa.

* * * * *

UNITED STATES PATENT AND TRADEMARK OFFICE
CERTIFICATE OF CORRECTION

PATENT NO. : 10,117,836 B2
APPLICATION NO. : 15/115026
DATED : November 6, 2018
INVENTOR(S) : Mary Ann Johnson et al.

It is certified that error appears in the above-identified patent and that said Letters Patent is hereby corrected as shown below:

In the Claims

At Column 16, Lines 43-57, Claim 1 please amend the structure for Formula I as follows:

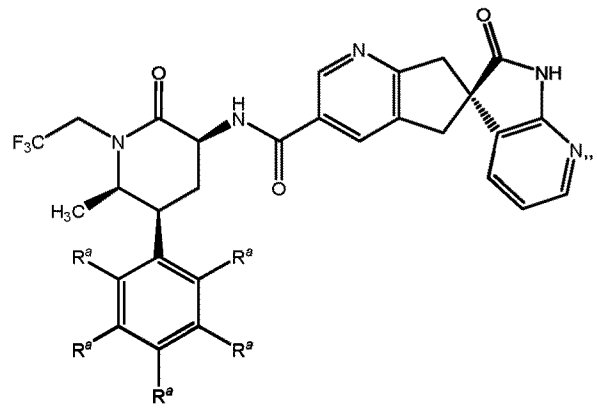

to be

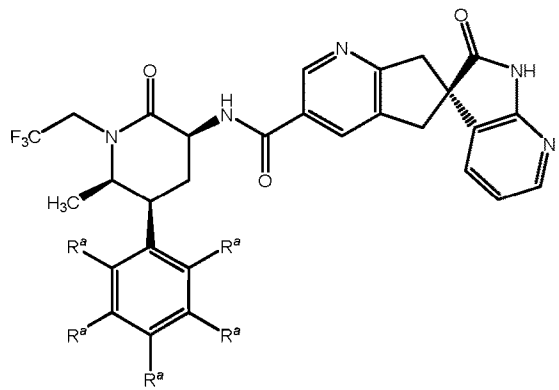

Signed and Sealed this
Twenty-ninth Day of January, 2019

Andrei Iancu
*Director of the United States Patent and Trademark Office*

At Column 17, Lines 12-24, Claim 4 please amend the structure for Formula Ia as follows:
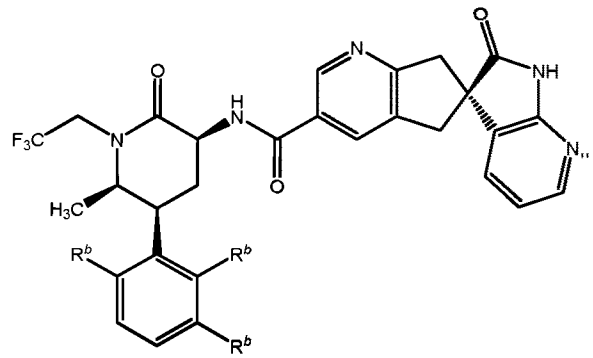
to be
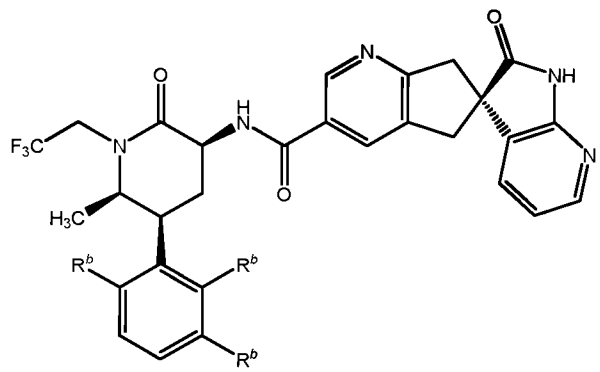
At Column 17, Lines 45-57, Claim 7 please amend the structure for Formula I as follows:
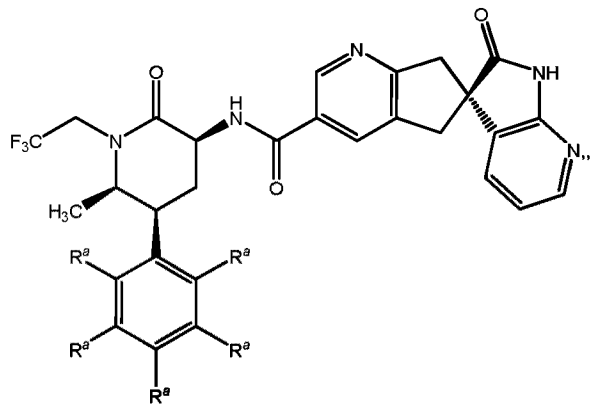
to be
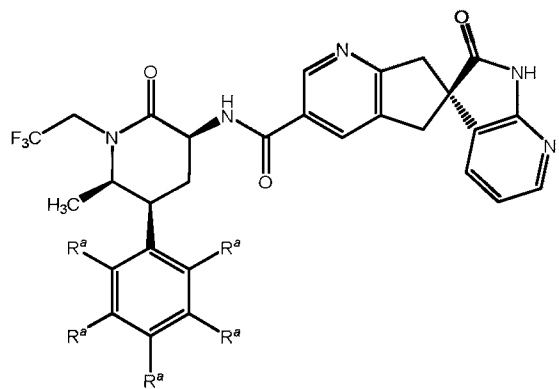

CERTIFICATE OF CORRECTION (continued)
U.S. Pat. No. 10,117,836 B2

At Column 17, Line 60, Claim 7:
"IV" should read --"$R^{a'}$"--

At Column 18, Lines 45-57, Claim 16 please amend the structure for Formula Ia as follows:

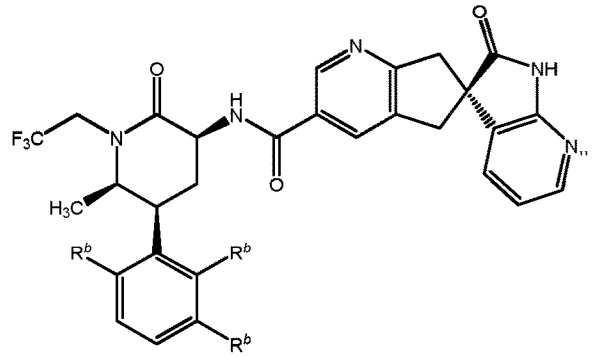

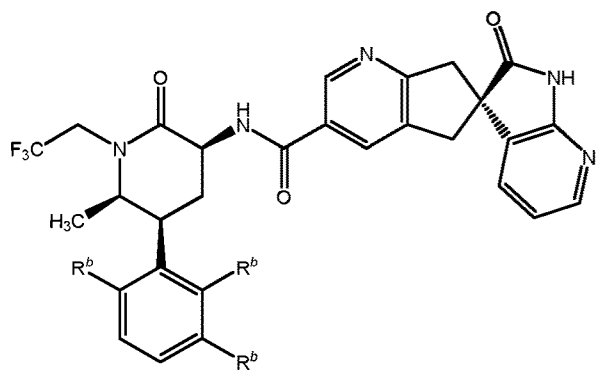

to be